United States Patent [19]
Jurewicz et al.

[11] 3,954,859

[45] May 4, 1976

[54] PREPARATION OF PHOSPHINE CHLORIDES

[75] Inventors: Anthony T. Jurewicz, Kendall Park; Warren W. Kaeding, Westfield, both of N.J.

[73] Assignee: Mobil Oil Corporation, New York, N.Y.

[22] Filed: Oct. 29, 1974

[21] Appl. No.: 518,923

Related U.S. Application Data

[63] Continuation-in-part of Ser. No. 419,842, Nov. 28, 1973, abandoned.

[52] U.S. Cl............................................. 260/543 P
[51] Int. Cl.$^2$............................................. C07F 9/34
[58] Field of Search................................... 260/543 P

[56] References Cited
UNITED STATES PATENTS

| | | | |
|---|---|---|---|
| 3,029,282 | 4/1962 | Toy | 260/543 P |
| 3,188,281 | 6/1965 | Buggman | 260/543 P |
| 3,200,145 | 8/1965 | Lutz | 260/543 P |
| 3,557,202 | 1/1971 | Stamm | 260/543 P |
| 3,709,932 | 1/1973 | Uhing | 260/543 P |
| 3,709,979 | 1/1973 | Chu | 423/328 |

*Primary Examiner*—Anton H. Sutto
*Attorney, Agent, or Firm*—Charles A. Huggett; Michael G. Gilman

[57] ABSTRACT

This specification discloses a process for reacting an unsaturated hydrocarbon with a phosphorus chloride. The unsaturated hydrocarbon may be aromatic hydrocarbons, such as benzene, toluene or xylene or ethylene. The phosphorous chloride for reacting with the aromatic is a phosphorous trihalide such as a phosphorous trichloride or a phosphine dihalide such as phenylphosphine dichloride. The phosphorus chloride for reacting with the ethylene is phosphorus trichloride. The reaction is carried out in the presence of, as a catalyst, a crystalline aluminosilicate zeolite in the hydrogen form having a silica to alumina ratio of at least 12 and a constraint index of 1 to 12. The reaction is carried out at a temperature of 147° C. to 475° C., sufficient to effect reaction of the unsaturated hydrocarbon with the phosphorus chloride. The reaction product obtained from benzene and phosphorus trichloride is phenylphosphine dichloride, from benzene and phenylphosphine dichloride is diphenylphosphine chloride, and from ethylene and phosphorus trichloride is vinylphosphine dichloride.

21 Claims, No Drawings

PREPARATION OF PHOSPHINE CHLORIDES

This application is a continuation-in-part of application Ser. No. 419,842 filed Nov. 28, 1973 now abandoned.

BACKGROUND OF THE INVENTION

1. Field of the Invention

This invention relates to the preparation of organic phosphine chlorides.

2. Description of the Prior Art

U.S. Pat. No. 3,210,418, issued Oct. 5, 1965, to John A. Pianfetti, discloses the preparation of phenylphosphine dichloride by reacting benzene at a temperature of 725° C. with phosphorus trichloride in the presence of oxygen as a catalyst.

An article in Biul. Wojskowej Akad. Tech. 13 (7/143), 109–15 (1964) (Pol) discloses the preparation of phenylphosphine dichloride and diphenylphosphine chloride by reacting benzene and phosphorus trichloride in the presence of aluminum chloride as a catalyst.

In an article in Organic Synthesis, 31, 88–90 (1951), there is disclosed the preparation of phenylphosphine dichloride comprising reacting phosphorus trichloride, benzene, aluminum chloride, and phosphorus oxychloride.

In an article in Zh. Obshch. Khim. 1968, 38(7), 1551–2 (Russ), there is disclosed the preparation of phenylphosphine dichloride by reacting phosphorus trichloride and benzene. The article discloses that in alternative experiments the reactor was filled with granulated alumina but results were not described.

U.S. Pat. No. 3,709,932 issued to Uhing discloses the reaction of lower alkenes and benzene at a temperature in excess of 350°C. with phosphorous trichloride in the presence of phosgene to produce a phosphonous dichloride. This patent issued Jan. 9, 1973.

In an article in J. Am. Chem. Soc., 77, 3526–9 (1955) there is described the preparation of diphenylphosphine chloride based on the reduction of diphenylphosphine trichloride with elemental phosphorous.

U.S. Pat. No. 3,702,886, issued Nov. 14, 1972, to Argauer et al., disclosed ZSM-5 catalyst.

U.S. Pat. No. 3,709,979, issued Jan. 9, 1973 to Chu, disclosed ZSM-11 catalyst.

West German Auslegeschrift No. 2,213,109 issued Sept. 21, 1972, discloses ZSM-12 catalyst.

Copending application Ser. No. 358,192, filed May 7, 1973, discloses ZSM-21 catalyst.

Copending application Ser. No. 130,442, filed Apr. 11, 1971, discloses TEA mordenite.

SUMMARY OF THE INVENTION

An unsaturated hydrocarbon selected from the group consisting of aromatic hydrocarbons, such as benzene, toluene or xylene, and ethylene is reacted with a phosphorous halide, such as a phosphorous chloride, the phosphorous halide selected for reaction with the aromatic being selected from the group consisting of phosphorous trichloride and phenylphosphine dichloride, and the phosphorous chloride being selected for reaction with the ethylene being phosphorous trichloride, by contacting the unsaturated hydrocarbon with the phosphorous chloride in the presence of, as a catalyst, a crystalline aluminosilicate zeolite in the hydrogen form having a silica to alumina ratio of at least 12 and a constraint index of 1 to 12, the contacting being at a temperature of 147° to 475° C. sufficient to effect reaction of the unsaturated hydrocarbon with the phosphorus chloride. It is considered to be within the scope of this invention to utilize other corresponding phosphorus halogen compound reactants such as, for example, the bromide analogues.

DESCRIPTION OF THE PREFERRED EMBODIMENTS

The process of the invention involves reacting an unsaturated hydrocarbon with a phosphorus chloride. The unsaturated hydrocarbon may be a benzene or it may be ethylene. Where the unsaturated hydrocarbon is benzene, the phosphorus chloride is phosphorus trichloride or is phenylphosphine dichloride. Where the unsaturated hydrocarbon is ethylene the phosphorus chloride is phosphorus trichloride. The reaction product of benzene and phosphorus trichloride is phenylphosphine dichloride. The reaction product of benzene and the phenylphosphine dichloride is diphenylphosphine chloride. The reaction product of the ethylene and the phosphorus trichloride is vinylphosphine dichloride.

The reaction of the unsaturated hydrocarbon with the phosphorus chloride is carried out by contacting the unsaturated hydrocarbon and the phosphorus chloride with the catalyst at a temperature of 147° C. to 475° C. However, the temperature within this range must be sufficient to effect reaction of the particular unsaturated hydrocarbon and the particular phosphorus chloride. The activities of the unsaturated hydrocarbons and the phosphorus chlorides differ and with the reactants having the greatest activities temperatures at the lower portion of the range may be employed while with the reactants having lesser activities temperatures at a higher portion of the range will be employed. Benzene and phosphorus trichloride having high activities and reaction can be effected at a temperature of 147° C. Any temperature up to 475° C. may be employed but temperatures in excess of 400° C. are not required. Benzene and phenylphosphine dichloride have lesser activities and the temperature of reaction should be at least 250° C. Again, any temperature up to 475° C. may be employed for these reactants. Ethylene and phosphorus trichloride have still lesser activities and the temperature of reaction should be at least 350° C. Still again, any temperature up to 475° C. can be employed for these reactants.

Phosphorus trichloride tends to decompose at high temperatures. While, when employing phosphorus trichloride as a reactant, temperatures as high as 475° C. can be employed, decomposition of the phosphorus trichloride is encountered. Decomposition is not so rapid that the reaction of phosphorus trichloride with the benzene or ethylene cannot be effected. However, the decomposition affects the economies of the process. Accordingly, where phosphorus trichloride is employed, it is preferred that the temperatures at which the phosphorus trichloride and the unsaturated hydrocarbon are contacted with the catalyst not be in excess of 450° C.

Contact of the phosphorus chloride and the unsaturated hydrocarbon with the catalyst is effected with the phosphorus chloride and the unsaturated hydrocarbon being in the vapor phase. The phosphorus chloride and the unsaturated hydrocarbon are heated to the desired reaction temperature within the range of 147° C. to 450° C. and, at atmospheric pressures and at these temperatures, the reactants will be in the vapor phase. The vaporized reactants are then contacted with the catalyst.

Contact of the vaporized reactants with the catalyst may be effected in any conventional manner. The reaction may be conducted as a batch operation or as a continuous operation. In carrying out the reaction as a batch reaction, the vaporized reactants and the catalyst may be contacted in a suitable closed reaction vessel for a time sufficient to effect a desired extent of reaction. This time, for example, may be 2 to 5 hours. The catalyst may be in the amount of 5–10% by weight of the reactants. The reaction, however, is preferably carried out as a continuous operation. In continuous operation, the vaporized reactants can be passed through a bed of the catalyst contained in a suitable reactor. In this type of operation, the volume hourly space velocity (VHSV) may be 0.19 to 0.50 volume of reactant per volume of catalyst per hour. Similarly, in a continuous operation, the vaporized reactants may be contacted with a moving or an ebullient bed of the catalyst.

In carrying out the reaction of the benzene with phosphorus trichloride, the temperatures employed, as stated above, may be 147° C. to 475° C. Within this temperature range, effective production of phenylphosphine dichloride on the basis of the amount of phosphorus trichloride converted to phenylphosphine dichloride is obtained. However, it is preferred to carry out the reaction at temperatures of 250° C. to 400° C. More preferably, the reaction is carried out at a temperature of 310° C.

The reaction of a benzene with phosphorus trichloride to form a phenylphosphine dichloride involves reaction of one mole of the benzene with one mole of the phosphorus trichloride. Thus, the reaction may be carried out employing one mole of the benzene for each mole of phosphorus trichloride. However, it is preferred to employ an excess of the benzene over phosphorus trichloride. Thus, it is preferred to carry out the reaction employing a molar ratio of the benzene to phosphorus trichloride of 3:1 to 10:1.

Following the reaction of the benzene with the phosphorus trichloride, the reaction product is treated for the recovery of the phenylphosphine dichloride. The reaction product may, for example, be condensed by cooling to room temperature in a water cooled condenser or other similar type of apparatus. The condensed liquid mixture may then be fractionated to obtain the desired product.

In carrying out the reaction of a benzene with phenylphosphine dichloride, the temperatures employed, as stated above, may be from 250° to 475° C. However, it is preferred that the temperature not be above 400° C. Thus, the reaction is preferably carried out at temperatures of 250° to 400° C.

The reaction of the benzene with the phenylphosphine dichloride to form a diphenylphosphine chloride involves reaction of one mole of a benzene with one mole of phenylphosphine dichloride. For this reaction, it is preferred, however, to employ an excess of the benzene over phenylphosphine dichloride. Thus, it is preferred to carry out the reaction employing a molar ratio of benzene to phenylphosphine dichloride of 3:1 to 10:1.

Following the reaction of the benzene with the phenylphosphine dichloride, the reaction product may be treated similarly as that from the reaction product of the benzene and phosphorus trichloride. Thus, the reaction product may be condensed. Thereafter, the condensed reaction product may be fractionated to recover the desired diphenylphosphine chloride.

It would appear from the foregoing descriptions of the reactions of benzene with phosphorus trichloride to produce phenylphosphine dichloride and of benzene with phenylphosphine dichloride to produce diphenylphosphine chloride that it would be possible to react benzene with phosphorus trichloride to produce diphenylphosphine chloride with or without mixture with phenylphosphine dichloride. However, this is not readily accomplished. The reaction of the benzene and the phosphorus trichloride is faster than the reaction of the benzene with the phenylphosphine dichloride as mentioned previously in connection with the reaction temperatures to be employed. Thus, reaction of the benzene with phenylphosphine dichloride does not occur as long as any phosphorus trichloride remains in the reaction mixture.

In carrying out the reaction of ethylene with phosphorus trichloride, the temperatures employed, as stated above, should be at least 350° C. The temperature may be as high as 475° C. However, it is preferred that the temperature not be in excess of 450° C.

The reaction of ethylene with phosphorus trichloride to form vinylphosphine dichloride involves one mole of ethylene with one mole of phosphorus trichloride. However, it is preferred to employ a molar excess of ethylene over phosphorus trichloride. Thus, it is preferred to carry out the reaction employing a molar ratio of ethylene to phosphorus trichloride of 3:1 to 10:1.

Following the reaction of the ethylene with the phosphorus trichloride, the reaction product may be treated for the recovery of the vinylphosphine dichloride. Thus, the reaction product may be cooled to condense the vinylphosphine dichloride. Thereafter, the condensed product may be fractionated to recover the vinylphosphine dichloride.

The unsaturated hydrocarbon and the phosphorus chloride are reacted by contacting the unsaturated hydrocarbon and the phosphorus chloride in the presence of, as a catalyst, a crystalline aluminosilicate zeolite in the hydrogen form having a silica to alumina ratio of at least 12 and a constraint index of 1 to 12. This catalyst will be hereinafter termed "the zeolite catalyst."

The zeolite catalyst has been recently discovered and comprises a class of crystalline aluminosilicate zeolites having some unusual properties. These zeolite catalysts induce profound transformations of aliphatic hydrocarbons to aromatic hydrocarbons in commercially desirable yields. Although they have unusually low alumina contents, i.e. high silica to alumina ratios, they are very active even when the silica to alumina ratio exceeds 30. The activity is surprising since the alumina in the zeolite framework is believed responsible for catalytic activity. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity.

An important characteristic of the crystal structure of this class of zeolites is that it provides constrained access to, and egress from, this intracrystalline free space by virtue of having a pore dimension greater than about 5 Angstroms and pore windows of about a size as would be provided by ten-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type of catalyst useful in this invention possesses, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic form within the channels. Although zeolite catalysts with a silica to alumina ratio of at least 12 are useful, it is preferred to use zeolite catalysts having higher ratios of at least about 30. The silica-alumina ratio may be as high as 300. Such zeolite catalysts, after activation, acquire an intracrystalline sorption capacity for normal hexane which is greater than that for water, i.e. they exhibit "hydrophobic" properties. It is believed that this hydrophobic character is advantageous in the present invention.

The zeolite catalysts useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by eight-membered rings of oxygen atoms, then access to molecules of larger cross-section than normal hexane is excluded and the zeolite is not of the desired type. Windows of ten-membered rings are preferred, although excessive puckering or pore blockage may render these catalysts ineffective. Twelve-membered rings do not generally appear to offer sufficient constraint to produce the advantageous conversions, although structures can be conceived, due to pore blockage or other cause, that may be operative.

Rather than attempt to judge from crystal structure whether or not a crystalline aluminosilicate zeolite possesses the necessary constrained access, a simple determination of the "constraint index" may be made by passing continuously a mixture of equal weight of normal hexane and 3-methylpentane over a small sample, approximately 1 gram or less, of the crystalline aluminosilicate zeolite at atmospheric pressure according to the following procedure. A sample of the crystalline aluminosilicate zeolite, in the form of pellets or extrudate, is crushed to a particle size about that of coarse sand and mounted in a glass tube. Prior to testing, the sample is treated with a stream of air at 1000° F. for at least 15 minutes. The sample is then flushed with helium and the temperature adjusted between 600° and 950° F. to give an overall conversion between 10% and 60%. The mixture of hydrocarbons is passed at 1 liquid hourly space velocity (i.e. 1 volume of hydrocarbon per volume of catalyst per hour) over the sample with a helium dilution to give a helium to total hydrocarbon mole ratio of 4:1. After 20 minutes on stream, a sample of the effluent is taken and analyzed, most conveniently by gas chromatography, to determine the fraction remaining unconverted for each of the two hydrocarbons.

The "constraint index" is calculated as follows:

$$\text{Constraint Index} = \frac{\log_{10}(\text{fraction of n-hexane unconverted})}{\log_{10}(\text{fraction of 3-methylpentane unconverted})}$$

The constraint index approximates the relative cracking rate constants for the two hydrocarbons. Crystalline aluminosilicate zeolites suitable for the present invention are those having a constraint index from 1.0 to 12.0, preferably 2.0 to 7.0.

In a preferred aspect of this invention, the catalysts hereof are selected as those having a crystal density, in the hydrogen form, of not substantially below about 1.6. It has been found that zeolites which satisfy all three of these criteria are most desired. Therefore, the preferred catalysts of this invention are those having a constraint index as defined above of about 1 to 12, a silica to alumina ratio of at least about 12 and a crystal density of not less than about 1.6. The dry density for known structures may be calculated from the number of silicon plus aluminum atoms per 1000 cubic Angstroms, as given, e.g. on page 11 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, is important as the locus of the catalytic activity.

The class of zeolite catalysts defined herein is exemplified, to the extent that they have a silica-alumina ratio between 12 and 300, by ZSM-5, ZSM-11, ZSM-12, ZSM-21, TEA mordenite and other similar materials.

The entire contents of recently issued U.S. Pat. No. 3,702,886 describing and claiming ZSM-5 are incorporated herein by reference.

ZSM-11 is more particularly described in U.S. Pat. No. 3,709,979, the entire contents of which are incorporated herein by reference.

ZSM-12 is more particularly described in U.S. Pat. 3,832,449, the entire contents of which are incorporated herein by reference.

ZSM-21 is more particularly described in U.S. Application Ser. No. 358,192 filed May 7, 1973, the entire contents of which are incorporated herein by reference.

TEA mordenite is more particularly described in U.S. Application Ser. No. 130,442 filed Apr. 11, 1971, the entire contents of which are incorporated herein by reference.

ZSM-5 can be identified, in terms of mole ratios of oxides, as follows:

$$0.9 \pm 0.3 \, M_{2/n} O : Al_2O_3 : bSiO_2 : zH_2O,$$

where M is a cation selected from the group consisting of a mixture of alkali metal cations, especially sodium, and tetraalkylammonium cations, the alkyl groups of which preferably contain 2–5 carbon atoms, $n$ is the valence of the cation, $b$ is at least 5 and preferably 15–300, and $z$ is from 0 to 40.

ZSM-11 can also be identified, in terms of mole ratios of oxides, as follows:

$$0.9 \pm 0.3 \, M_{2/n} O : Al_2O_3 : bSiO_2 : zH_2O,$$

where M and $n$ are as defined above, $b$ is from 20 to 90, and $z$ is from 6 to 12.

ZSM-12 can also be identified, in terms of mole ratios of oxides, as follows:

$$1.0 \pm 0.4 \, M_{2/n} O : Al_2O_3 : bSiO_2 : zH_2O,$$

where M and $n$ are as defined above, $SiO_2$ is from 20 to 100, and $z$ is 0 to 60.

The zeolite catalysts can be suitably prepared from a solution containing water, tetrapropyl ammonium hydroxide and the elements of sodium oxide, an oxide of aluminum and an oxide of silica. This mixture, a gel, is maintained at reaction conditions until the crystals of the zeolite are formed. Thereafter, the crystals are separated from the liquid and recovered. Typical reaction conditions consist of a temperature of from about 75° to 175° C. for a period of about six hours to 60 days. A more preferred temperature range is from about 90° to 150° C., with the amount of time at a temperature in such a range being from about 12 hours to 20 days.

The digestion of the gel particles is carried out until crystals form. The solid product is separated from the reaction medium, as by cooling the whole to room temperature, filtering and water washing.

The specific crystalline aluminosilicate zeolites when prepared in the presence of organic cations are catalytically inactive, possibly because the intracrystalline free space is occupied by organic cations from the forming solution. They may be activated by heating in an inert atmosphere at 1000° F., for example, under nitrogen for one hour. The presence of organic cations in the forming solution may not be absolutely essential to the formation of the zeolite catalyst; however, the presence of these cations does appear to favor the formation of the zeolite catalyst.

The crystalline aluminosilicate zeolites can be converted to the hydrogen form generally by two methods. The first involves direct ion exchange employing an acid. Suitable acids include both inorganic acids and organic acids. Typical inorganic acids which can be employed include hydrochloric acid, hypochlorous acid, sulfuric acid, sulfurous acid, hydrosulfuric acid, nitric acid, nitrous acid, hyponitrous acid, phosphoric acid, and carbonic acid. Typical organic acids which can be employed are the monocarboxylic and polycarboxylic acids which can be aliphatic, aromatic, or cycloaliphatic in nature. Representative suitable acids include acetic, trichloroacetic, bromoacetic, citric, maleic, fumaric, itaconic, phenylacetic, benzene sulfonic and methane sulfonic acids. The second method for preparing the hydrogen form, which is preferred, involved first preparing an ammonium or other hydrogen ion precursor form by base exchange and then calcining to cause evolution of the ammonia leaving a hydrogen ion remaining on the zeolite. Calcining is carried out in air at 1000° F. for about 15 minutes to about 24 hours. Suitable compounds for preparing the hydrogen ion precursor form include ammonium compounds such as the chloride, bromide, iodide, bicarbonate, sulfate, citrate, borate, and palmitate. Still other ammonium compounds which can be employed include quaternary ammonium compounds such as tetramethylammonium hydroxide and trimethylammonium chloride. Where this second method of preparing the hydrogen form is employed the activation by heating in an inert atmosphere described above may be eliminated.

Natural zeolites may sometimes be converted to the zeolite catalyst by various activation procedures and other treatments such as base exchange, steaming, alumina extraction and calcination, in combinations. Natural minerals which may be so treated include ferrierite, brewsterite, stilbite, dachiardite and epistilbite. The preferred zeolite catalysts are ZSM-5, ZSM-11, ZSM-12, ZSM-21 and TEA mordenite, wih ZSM-5 particularly preferred.

A porous matrix can be employed together with the zeolite catalyst. The catalyst can be incorporated, combined, dispersed, or otherwise intimately admixed with the porous matrix in such proportions that resulting products contain from 1% to 95% by weight and preferably from 10% to 70% by weight of the zeolite catalyst in the final composite.

The term "porous matrix" includes inorganic compositions of which the zeolites can be incorporated, combined, dispersed, or otherwise intimately admixed wherein the matrix may be catalytically active or inactive. It is to be understood that the porosity of the composition employed as a matrix can be either inherent in the particular material or it can be introduced by mechanical or chemical means. Representative of matrices which can be employed include metals and alloys thereof, sintered metals, and sintered glass, asbestos, silicon carbide, aggregates, pumice, firebrick, diatomaceous earths, alumina and inorganic oxides. Inorganic compositions, especially those comprising alumina and those of a siliceous nature, are preferred. Of these matrices, inorganic oxides such as clay, chemically treated clays, silica, silica alumina, etc., as well as alumina, are particularly preferred because of their superior porosity, attrition resistance and stability.

Techniques for incorporating the zeolite catalyst into a matrix are conventional in the art and are set forth in U.S. Pat. No. 3,140,253.

The following examples will be illustrative of the invention.

EXAMPLE 1

This example will illustrate the reaction of benzene with phosphorus trichloride.

The catalyst employed was ZSM-5 in the hydrogen form. The catalyst was obtained in powder form and prior to being used was pressed into a wafer, the wafer was crushed, and the crushed wafer was screened to 8-14 mesh. The screened catalyst was then dried in air at 500° C.

The reactor was charged with 20 cubic centimeters of the catalyst and the catalyst was positioned in the reactor by means of quartz wool plugs. The reactor was constructed of glass and was approximately 1.5 centimeters in diameter and approximately 20 centimeters in length not counting the end fittings. The reactor contained a removable thermowell in the center which accommodated a plurality of thermocouples to measure the temperature in various parts of the catalyst bed. The top inlet was provided with an opening for admitting the feed.

The feed to the reactor contained a mixture of benzene and phosphorus trichloride in the ratio of 3 moles of benzene to each mole of phosphorus trichloride. The rate at which the mixture of benzene and phosphorus trichloride was passed to the reactor was varied from time to time throughout the reaction. The feed also contained nitrogen as a carrier gas but the rate at which the nitrogen was fed to the reactor was maintained constant at 40 milliliters per minute regardless of the rate of the mixture of benzene and phosphorus trichloride. The feed was heated to the reaction temperature, and the benzene and phosphorus trichloride was vaporized by passing through an electrically heated glass furnace.

The reaction was carried out in a number of stages. In each stage, a different combination of temperature, rate of feed of reactants, liquid hourly space velocity (LHSV) was employed. Between the 5th and 6th stages, the reaction was discontinued and nitrogen at 270° C. was passed over the catalyst overnight. Between the 8th and 9th stages, air at 500° C. was passed over the catalyst overnight. Between the 12th and 13th stages, air at 500° C. was passed over the catalyst over the weekend.

The liquid product was obtained by passing the effluent gases through a reservoir cooled to 5° C. by water and then through a dry ice trap. The remaining effluent gas was passed through a wet test meter to measure the volume and was finally collected in a tower by displacement by water. For most of the stages, the liquid product was analyzed by gas chromatography to determine the conversion of phosphorus trichloride and the selectivity to phenylphosphine dichloride.

The table gives the results obtained. In the table, ml/hr signifies milliliters per hour, ml/min signifies milliliters per minute and the material balances, conversions of phosphorus trichloride, and selectivities to phenylphosphine dichloride ($\phi$-$PCl_2$) and others are given in percent.

TABLE I

| Stage | 1 | 2 | 3 | 4 | 5 | 6 | 7 | 8 | 9 | 10 | 11 | 12 | 13 |
|---|---|---|---|---|---|---|---|---|---|---|---|---|---|
| Temp, °C | 147 | 172 | 207 | 235 | 270 | 297 | 330 | 270 | 260 | 295 | 320 | 340 | 258 |
| Reactor Feed | | | | | | | | | | | | | |
| benzene-$PCl_3$(ml/hr) | 8.3 | 8.3 | 6.8 | 9.8 | 9.2 | 10.8 | 12.0 | 10.6 | 10.4 | 6.4 | 7.6 | 9.8 | 11 |
| $N_2$(ml/min) | 40 | 40 | 40 | 40 | 40 | 40 | 40 | 40 | 40 | 40 | 40 | 40 | 40 |
| Material Balance | 86 | 87 | 82 | 87 | 88 | 94 | 91 | 87 | 84 | 87 | 88 | 87 | 49 |
| $PCl_3$ Conversion | 1.7 | 1.1 | 10 | 15 | 19 | 0 | 5.5 | — | 10 | 9.5 | 6.6 | 3 | 0.7 |
| Selectivity | | | | | | | | | | | | | |
| $\phi$ — $PCl_2$ | 100 | 100 | 98 | 95 | 99 | — | 90 | — | 99 | 98 | 95 | 80 | 80 |
| Others | — | — | 2 | 5 | 1 | — | 10 | — | 1 | 2 | 5 | 20 | 20 |
| LHSV | 0.42 | 0.42 | 0.34 | 0.49 | 0.46 | 0.54 | 0.60 | 0.53 | 0.52 | 0.32 | 0.38 | 0.49 | 0.55 |

EXAMPLE 2

This example will also illustrate the reaction of benzene with phosphorus trichloride.

The catalyst employed in this example was ZSM-5 in the hydrogen form. However, this catalyst, obtained as a powder, was in admixture with alumina as a matrix. The alumina constituted 35% by weight of the combined alumina and catalyst. The catalyst as obtained was pressed into a wafer, crushed, screened, and dried similarly to the catalyst in Example 1. The reaction was carried out in stages and in the same type of reactor as in Example 1. Between the 6th and 7th stages, air at 500° C. was passed over the catalyst overnight.

The table gives the results obtained.

TABLE II

| Stage | 1 | 2 | 3 | 4 | 5 | 6 | 7 |
|---|---|---|---|---|---|---|---|
| Temp, °C | 261 | 284 | 310 | 345 | 380 | 310 | 305 |
| Reactor Feed | | | | | | | |
| benzene-$PCl_3$(ml/hr) | 10.4 | 10 | 10 | 8.6 | 8.4 | 7.8 | 8.6 |
| $N_2$(ml/min) | 40 | 40 | 40 | 40 | 40 | 40 | 40 |
| Material Balance | 85 | 85 | 86 | 96 | 86 | 85 | 85 |
| $PCl_3$ Conversion | 17 | 21 | 23 | 15 | 16.5 | 2.1 | 17 |
| Selectivity | | | | | | | |
| $\phi$ — $PCl_2$ | 99 | 99 | 99 | 99 | 99 | 96 | 99 |
| Others | 1 | 1 | 1 | 1 | 1 | 4 | 1 |
| LHSV | 0.52 | 0.50 | 0.50 | 0.43 | 0.42 | 0.39 | 0.43 |

EXAMPLE 3

This example will also illustrate the reaction of benzene with phosphorus trichloride.

The reaction of this example was carried out in the same manner and in the same type of reactor as in the previous two examples. However, the catalyst was the same type as that employed in Example 2. Further, however, the temperature employed in each stage was the same, namely, 310° C.

The table gives the results obtained.

TABLE III

| Stage | 1 | 2 | 3 | 4 | 5 | 6 | 7 | 8 | 9 | 10 | 11 | 12 | 13 |
|---|---|---|---|---|---|---|---|---|---|---|---|---|---|
| Temp, °C | 310 | 310 | 310 | 310 | 310 | 310 | 310 | 310 | 310 | 310 | 310 | 310 | 310 |
| Reactor Feed | | | | | | | | | | | | | |

TABLE III-continued

| Stage | 1 | 2 | 3 | 4 | 5 | 6 | 7 | 8 | 9 | 10 | 11 | 12 | 13 |
|---|---|---|---|---|---|---|---|---|---|---|---|---|---|
| benzene-$PCl_3$(ml/hr) | 8.9 | 8.1 | 7.7 | 7.5 | 7.0 | 6.9 | 6.9 | 11.6 | 11.0 | 10.4 | 9.8 | 9.3 | 8.8 |
| $N_2$ (ml/min) | 40 | 40 | 40 | 40 | 40 | 40 | 40 | 40 | 40 | 40 | 40 | 40 | 40 |
| Material Balance | 84 | 85 | 85 | 86 | 89 | 82 | 87 | 88 | 89 | 89 | 87 | 90 | 86 |
| $PCl_3$ Conversion | 20 | 25 | 20 | 17.5 | 14 | 12 | 10.5 | 20 | 13.5 | 12 | 8 | 7.5 | 6 |
| Selectivity | | | | | | | | | | | | | |
| $\phi - PCl_2$ | 100 | 87 | 95 | 93 | 80 | 71 | 58 | 98 | 98 | 95 | 93 | 84 | 74 |
| Others | — | 13 | 5 | 7 | 20 | 29 | 42 | 2 | 2 | 5 | 7 | 16 | 26 |
| LHSV | 0.45 | 0.40 | 0.38 | 0.38 | 0.35 | 0.35 | 0.35 | 0.58 | 0.55 | 0.52 | 0.49 | 0.47 | 0.44 |
| Time on Stream, minutes | 31 | 60 | 87.3 | 120 | 188 | 233 | 287 | 30 | 60 | 90 | 120 | 180 | 240 |

EXAMPLE 4

This example will also illustrate the reaction of benzene with phosphorus trichloride.

The reaction of this example was carried out similarly to the reaction of Example 1 and in the same type of reactor. The catalyst, however, was the same type as that employed in Example 2. Further, however, the molar ratio of benzene to phosphorus trichloride in the reactor feed was 10 to 1.

The table gives the results obtained.

TABLE IV

| Stage | 1 | 2 | 3 | 4 | 5 |
|---|---|---|---|---|---|
| Temp, °C | 247 | 288 | 314 | 360 | 380 |
| Reactor Feed | | | | | |
| benzene-$PCl_3$(ml/hr) | 5.2 | 5.8 | 5.2 | 6.0 | 6.0 |
| $N_2$ (ml/min) | 40 | 40 | 40 | 40 | 40 |
| Material Balance | 65 | 76 | 80 | 74 | 78 |
| $PCl_3$ Conversion | 100 | 29 | 42.5 | 45.7 | 42 |
| Selectivity | | | | | |
| $\phi - PCl_2$ | — | 78 | 92 | 86 | 80 |
| Others | — | 22 | 8 | 14 | 20 |
| LHSV | 0.26 | 0.29 | 0.26 | 0.30 | 0.30 |

EXAMPLE 5

This example will illustrate the reaction of benzene with phenylphosphine dichloride.

The reaction of this example was carried out by passing the feed containing benzene and phenylphosphine dichloride along with the nitrogen through the same type of reactor, although constructed of quartz, and the in the same manner as in the previous examples. The feed contained the benzene and the phenylphosphine dichloride in the weight ratio of 56.6 grams of benzene to 33.4 grams of phenylphosphine dichloride. The catalyst was the same as that employed in Example 2. Between the 5th and 6th stages, air at 500° C. was passed over the catalyst overnight.

The table gives the results obtained. In this table, $0_2$ — PCl signifies diphenylphosphine chloride.

EXAMPLE 6

This example will illustrate the reaction of ethylene with phosphorus trichloride.

Ethylene, at a rate of 100 ml/min and $PCl_3$, at a rate of 15 ml/hr was fed to a vapor phase reactor bed containing 20.0 cc (12.8 grams) of ZSM-5 catalyst in the hydrogen form (35% $Al_2O_3$ binder), at a temperature of 410° C. A product was obtained with a 25% selectivity and 1% conversion, which was identified as vinyl phosphorus dichloride, by conversion to a stable derivative. The latter was $(CH_2=CH)P(O)(OCH_2CH_2Cl)_2$ prepared by treatment with excess ethylene oxide, followed by careful oxidation with $N_2O_4$ gas, in $CH_2Cl_2$ solution. The derivative was identical with an authentic standard.

EXAMPLES 7 – 14

REACTION OF AROMATIC COMPOUNDS WITH $PCl_3$ OVER HZSM-5

A quartz, tubular reactor, fitted with a thermowell in the center for temperature measurement, was filled with 9.0 gm (24 cc) of 6-8 mesh, pelletized HZSM-5. A syringe pump was used to feed a 3 to 1 molar mixture of aromatic hydrocarbon/phosphorus trichloride solution to the preheater where it was vaporized and led to the catalyst bed. The products were condensed in a cold water, jacketed receiver. A slow stream of dry nitrogen was used as a carrier.

TABLE V

| Stage | 1 | 2 | 3 | 4 | 5 | 6 | 7 | 8 | 9 | 10 | 11 |
|---|---|---|---|---|---|---|---|---|---|---|---|
| Temp, °C | 225 | 260 | 290 | 320 | 360 | 420 | 428 | 450 | 483 | 515 | 540 |
| Reactor Feed | | | | | | | | | | | |
| benzene-$\phi PCl_2$(ml/hr) | 14.2 | 6.8 | 3.8 | 5.8 | 4.8 | 3.8 | 9.2 | 6.6 | 4.2 | 2.7 | 1.7 |
| $N_2$(ml/min) | 40 | 40 | 40 | 40 | 40 | 40 | 40 | 40 | 40 | 40 | 40 |
| Material Balance | 82 | 94 | 88 | 81 | 83 | 79 | 78 | 89 | 86 | 71 | 47 |
| $\phi$-$PCl_2$ Conversion | 8.5 | 6.5 | 8.0 | 15 | 12 | 21 | 19 | 13 | 16 | — | — |
| Selectivity | | | | | | | | | | | |
| $\phi_2 - PCl$ | — | 16 | 20 | 22 | 15 | 49 | 26 | 51 | 63 | — | — |
| Others | 100 | 84 | 80 | 78 | 85 | 51 | 75 | 49 | 37 | — | — |
| LHSV | 0.71 | 0.34 | 0.19 | 0.29 | 0.24 | 0.19 | 0.46 | 0.33 | 0.21 | 0.14 | 0.09 |

The liquid products were analyzed by gas chromatography.

Phenylphosphine dichloride, $C_6H_5PCl_2$, was the only product detected when benzene and $PCl_3$ were fed to the catalytic reactor. A mixture of o, m, and p-tolylphosphine dichloride, $CH_3C_6H_4PCl_2$, was the only organic product detected when toluene and $PCl_3$ were used as the starting material. A small amount, < 1%, of $POCl_3$ was observed. A mixture of α- and β-naphthylphosphine dichloride, $C_{10}H_7PCl_2$, was produced, along with a small amount of $POCl_3$ when naphthalene and $PCl_3$ were used as the feed. A small amount of 2,5, dimethyl phenylphosphine dichloride was detected when p-xylene and $PCl_3$ were used as the feed. Traces of toluene, $POCl_3$ and an unidentified product were observed with the latter. The results are summarized in more detail in Table VI.

TABLE VI

| Example No. | Feed Moles | Temp. °C. | WHSV | $PCl_3$ Conversion,% | Selectivity to $ArPCl_2$,% | |
|---|---|---|---|---|---|---|
| 7 | 3 Benzene 1 $PCl_3$ | 300 | 2.2 | 18.2 | 100 | |
| 8 | 3 Benzene 1 $PCl_3$ | 300 | 2.2 | 14.0 | 100 | |
| 9 | 3 p-xylene 1 $PCl_3$ | 300 | 2.1 | 0.6 | 35 | |
| 10 | 3-p-xylene 1 $PCl_3$ | 300 | 2.1 | 0.2 | 60 | |
| 11 | 3 Toluene 1 $PCl_3$ | 300 | 2.0 | 8.4 | o,m 50 | p 50 |
| 12 | 3 Toluene 1 $PCl_3$ | 300 | 2.0 | 9.1 | 22 | 78 |
| 13 | 3 Toluene 1 $PCl_3$ | 300 | 2.0 | 2.8 | 18 | 82 |
| 14 | 2 Naphthalene 1 $PCl_3$ | 300 | 2.0 | 5.5 | $\frac{\alpha + \beta}{95}$ | |

What is claimed is:

1. The process for reacting an unsaturated hydrocarbon selected from the group consisting of a benzene aromatic hydrocarbon and ethylene with a phosphorous halide, the phosphorous halide for reacting with the aromatic hydrocarbon being selected from the group consisting of phosphorous trihalide and phenylphosphine dihalide and the phosphorous halide for reacting with the ethylene being phosphorous trihalide, which comprises contacting said unsaturated hydrocarbon with said phosphorous halide in the presence of, as a catalyst, a crystalline aluminosilicate zeolite in the hydrogen form having a silica to alumina ratio of at least 12 and a constraint index of 1 to 12, said contacting being at a temperature of 147° to 475°C sufficient to effect reaction of said unsaturated hydrocarbon with said phosphorous halide.

2. The process of claim 1 wherein the molar ratio of said unsaturated hydrocarbon to said phosphorous halide is 3:1 to 10:1.

3. The process of claim 1 wherein said catalyst is ZSM-5 in the hydrogen form, which has a mole ratio of oxides, as follows: $0.9 \pm 0.3$ $M_2/m$ $O:Al_2O_3:bSiO_2:zH_2O$, where M is mixed alkali metal cations and tetraalkyl ammonium cations, the alkyl groups of which preferably contain 2–5 carbon atoms, n is the valence of the cation, b is at least 5 and preferably 15-300, and z is from 0 to 40.

4. The process of claim 1 for the preparation of phenylphosphine dichloride comprising contacting said benzene aromatic hydrocarbons with phosphorous trichloride in the presence of, as a catalyst, a crystalline aluminosilicate zeolite in the hydrogen form having a silica to alumina ratio of at least 12 and a constraint index of 1 to 12.

5. The process of claim 4 wherein said contacting is at a temperature of 250° to 400°C.

6. The process of claim 4 wherein said contacting is at a temperature of 310°C.

7. The process of claim 4 wherein the molar ratio of said benzene to said phosphorous trichloride is 3:1 to 10:1.

8. The process of claim 4 wherein said catalyst is ZSM-5 in the hydrogen form.

9. The process of claim 4 wherein said contacting is at a temperature of 250° to 400°C., the molar ratio of said benzene aromatic hydrocarbon to said phosphorous trichloride is 3:1 to 10:1, and said catalyst is ZSM-5 in the hydrogen form which has a mole ratio of oxides, as follows: $0.9 \pm 0.3$ $M_2/n$ $O:Al_2O_3:bSiO_2:zH_2O$, where M is a mixture of alkali metal cations, and tetraalkylammonium cations, the alkyl groups of which preferably contain 2–5 carbon atoms, n is the valence of the cation, b is at least 5 and preferably 15-300, and z is from 0 to 40.

10. The process of claim 1 for the preparation of diphenylphosphine monochloride comprising contacting said aromatic hydrocarbon aromatic hydrocarbons with phenylphosphine dichloride in the presence of, as a catalyst, a crystalline aluminosilicate zeolite in the hydrogen form having a silica to alumina ratio of at least 12 and a constraint index of 1 to 12.

11. The process of claim 10 wherein said contacting is at a temperature of 250° to 400°C.

12. The process of claim 10 wherein the molar ratio of said benzene aromatic hydrocarbon to said phenylphosphine dichloride is 3:1 to 10:1.

13. The process of claim 10 wherein said catalyst is ZSM-5 in the hydrogen form.

14. The process of claim 1 wherein said contacting is at a temperature of 250° to 400°C., the molar ratio of said benzene aromatic hydrocarbon to said phenylphosphine dichloride is 3:1 to 10:1, and said catalyst is ZSM-5 in the hydrogen form which has a mole ratio of oxides, as follows:

$0.9 \pm 0.3$ $M_{2/n}O:Al_2O_3:bSiO_2:zH_2O$, where M is a mixture of alkali metal cations, and tetraalkyl ammonium cations, the alkyl groups of which preferably contain 2–5 carbon atoms, $n$ is the valence of the cation, $b$ is at least 5 and preferably 15-300, and $z$ is from 0 to 40.

15. The process of claim 1 for the preparation of vinylphosphine dichloride comprising contacting ethylene with phosphorous trichloride in the presence of, as a catalyst, a crystalline aluminosilicate zeolite in the hydrogen form having a silica to alumina ratio of at least 12 and a constraint index of 1 to 12.

16. The process of claim 15 wherein said contacting is at a temperature of 350° to 450°C.

17. The process of claim 15 wherein the molar ratio of said ethylene to said phosphorous trichloride is 3:1 to 10:1.

18. The process of claim 15 wherein said catalyst is ZSM-5 in the hydrogen form.

19. The process of claim 15 wherein said contacting is at a temperature of 350° to 450°C., the molar ratio of said ethylene to said phosphorous trichloride is 3:1 to 10:1, and said catalyst is ZSM-5 in the hydrogen form.

20. The process of claim 1 wherein said catalyst has a crystal density of not less than about 1.6 grams per cubic centimeter.

21. The process claimed in claim 1 wherein said benzene aromatic hydrocarbon is at least one member selected from the group consisting of benzene, toluene, xylene and naphthalene.

\* \* \* \* \*